(12) United States Patent
Hatcher et al.

(10) Patent No.: US 8,523,764 B2
(45) Date of Patent: Sep. 3, 2013

(54) REMOTE VIEWING APPARATUS

(75) Inventors: Clifford Hatcher, Orlando, FL (US); Gary L. Hensley, Irwin, PA (US)

(73) Assignee: Siemens Energy, Inc., Orlando, FL (US)

(*) Notice: Subject to any disclaimer, the term of this patent is extended or adjusted under 35 U.S.C. 154(b) by 1648 days.

(21) Appl. No.: 11/602,833

(22) Filed: Nov. 21, 2006

(65) Prior Publication Data
US 2007/0129604 A1 Jun. 7, 2007

Related U.S. Application Data

(60) Provisional application No. 60/748,082, filed on Dec. 7, 2005.

(51) Int. Cl.
*A61B 1/00* (2006.01)
(52) U.S. Cl.
USPC ............................ 600/136; 600/131; 600/146
(58) Field of Classification Search
USPC .................................................. 600/136, 132
See application file for complete search history.

(56) References Cited

U.S. PATENT DOCUMENTS

| | | | |
|---|---|---|---|
| 4,253,447 A | 3/1981 | Moore et al. | |
| 4,491,865 A | 1/1985 | Danna et al. | |
| 4,840,474 A | 6/1989 | Heft et al. | |
| 4,919,112 A * | 4/1990 | Siegmund | 600/136 |
| 4,937,675 A | 6/1990 | Starceski et al. | |
| 4,941,456 A | 7/1990 | Wood et al. | |
| 4,998,182 A | 3/1991 | Krauter et al. | |
| 5,243,967 A * | 9/1993 | Hibino | 600/109 |
| 5,323,899 A * | 6/1994 | Strom et al. | 206/363 |
| 5,373,317 A * | 12/1994 | Salvati et al. | 348/65 |
| 5,670,879 A | 9/1997 | Zombo et al. | |
| 5,846,183 A * | 12/1998 | Chilcoat | 600/136 |
| 5,928,137 A * | 7/1999 | Green | 600/160 |
| 6,066,089 A * | 5/2000 | Costello et al. | 600/102 |
| 6,163,378 A | 12/2000 | Khoury | |
| 6,198,280 B1 | 3/2001 | Hensley et al. | |
| 6,229,563 B1 | 5/2001 | Miller, II et al. | |
| 6,371,907 B1 * | 4/2002 | Hasegawa et al. | 600/146 |
| 6,487,922 B1 | 12/2002 | Bauer et al. | |
| 6,506,150 B1 * | 1/2003 | Ouchi | 600/132 |
| 6,554,766 B2 * | 4/2003 | Maeda et al. | 600/132 |
| 6,589,165 B2 | 7/2003 | Bodor et al. | |
| 6,626,824 B2 | 9/2003 | Ruegg et al. | |
| 6,666,818 B2 | 12/2003 | Dhindsa | |
| 6,692,431 B2 | 2/2004 | Kazakevich | |
| 6,697,164 B1 | 2/2004 | Babayoff et al. | |
| 6,793,622 B2 * | 9/2004 | Konomura et al. | 600/152 |
| 6,814,169 B2 | 11/2004 | Moore et al. | |
| 7,074,182 B2 * | 7/2006 | Rovegno | 600/131 |
| 7,108,656 B2 * | 9/2006 | Fujikawa et al. | 600/102 |
| 7,285,088 B2 * | 10/2007 | Miyake | 600/152 |
| 7,422,559 B2 * | 9/2008 | Kehoskie et al. | 600/140 |

(Continued)

*Primary Examiner* — Matthew J Kasztejna

(57) ABSTRACT

A remote viewing device including a hand-holdable control unit. The control unit supports a display device and a drive assembly. The drive assembly is removably attached to the control unit and provides mechanical power to an insertion tube. A distal end of the insertion tube includes an inspection head for insertion into a structure for imaging the interior of the structure. The insertion tube is removably attached to the drive assembly by a connector assembly, where the connector assembly is operable, when attached, to convey mechanical power from the drive assembly for moving the articulated tip in response to a user input at the control unit, and to convey images from the inspection head to the display device.

12 Claims, 3 Drawing Sheets

(56) References Cited

U.S. PATENT DOCUMENTS

| | | | |
|---|---|---|---|
| 2002/0026096 A1* | 2/2002 | Motoki et al. | 600/146 |
| 2002/0103418 A1* | 8/2002 | Maeda et al. | 600/132 |
| 2003/0125607 A1* | 7/2003 | Boebel et al. | 600/136 |
| 2004/0183900 A1 | 9/2004 | Karpen et al. | |
| 2005/0050707 A1 | 3/2005 | Scott et al. | |
| 2005/0129108 A1 | 6/2005 | Bendall et al. | |
| 2006/0052664 A1* | 3/2006 | Julian et al. | 600/146 |

* cited by examiner

REMOTE VIEWING APPARATUS

CROSS-REFERENCE TO RELATED APPLICATIONS

This application claims the benefit of U.S. Provisional Application No. 60/748,082, filed Dec. 7, 2005, which is incorporated herein by reference.

FIELD OF THE INVENTION

This invention relates generally to the field of non-destructive examination, and more particularly to vision systems for remote viewing of inaccessible test areas.

BACKGROUND OF THE INVENTION

A variety of remote viewing devices are known for performing visual inspections in generally inaccessible test areas. Borescopes, endoscopes and laparoscopes are examples of remote viewing devices that incorporate a small light-gathering device at the distal end of an elongated inspection tube that is inserted through a small opening to reach a remote viewing area. The light-gathering device may be a fiber optic cable that transmits the gathered light through the inspection tube to a receiving device at the proximal end of the inspection tube, or it may be a camera that transmits a video signal through the inspection tube to a display located remote from the viewing area.

U.S. Pat. No. 5,373,317, incorporated by reference herein, describes a borescope that may be used for inspecting restricted areas of a component such as a turbine or electrical generator without necessitating the disassembly of the component. The borescope of the '317 patent includes a hand-held control unit incorporating a joystick that functions to control an articulated tip at a distal end of an insertion tube. The control unit also includes a video display device for providing images of a test area collected by a video camera forming part of a viewing head attached to the articulated tip. A light source provides light to the test area via a fiber optic bundle that passes through the hand-held control unit and the insertion tube to the viewing head. The servomotors that move the articulated tip in response to control of the joystick are also mounted within a proximal end of the control unit to provide a balanced construction to the hand-held control unit.

SUMMARY OF THE INVENTION

In accordance with one aspect of the invention, a remote viewing device is provided comprising a hand-holdable control unit, and a display device mounted to the control unit. A drive assembly is removably attached to the control unit for providing mechanical power. The device further includes an insertion tube comprising a proximal end and an articulated tip at a distal end. An inspection head is associated with the articulated tip, the inspection head being configured for imaging the interior of an object. A connector assembly removably interconnects the control unit and the proximal end of the insertion tube. The connector assembly is operable, when connected, to convey the mechanical power from the drive assembly for moving the articulated tip in response to a user input at the control unit, and to convey images from the inspection head to the display device.

In accordance with another aspect of the invention, a remote viewing device is provided comprising a hand-holdable control unit, and a display device mounted to the control unit. A drive assembly is provided for providing mechanical power. The device further includes an insertion tube comprising a proximal end and an articulated tip at a distal end. An inspection head is associated with the articulated tip, the inspection head being configured for imaging the interior of an object. A connector assembly removably interconnects the control unit and the proximal end of the insertion tube. The connector assembly is operable, when connected, to convey images from the inspection head to the display device.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

DETAILED DESCRIPTION OF THE INVENTION

A prior art borescope as described in U.S. Pat. No. 5,373,317 is susceptible to failure as a result of the failure of any of its constituent parts, most notably the fiber optic cable, camera, articulated tip, insertion tube, electronics and servomotors. The present inventors have recognized that the expense of using, maintaining and repairing prior art borescopes is increased because the borescopes are assembled as integrated units. Further, when planning for the inspection of an industrial component such as an electrical generator or a gas or steam turbine, the user must anticipate the areas to be inspected and must select a borescope that is capable of penetrating the component to reach the desired test areas to provide the desired image.

Two key variables that are considered during inspection planning are the length of the insertion tube and the diameter of the insertion tube. An insertion tube that is too short to reach the test area from the access point is obviously problematic, and thus a borescope having an insertion tube that is longer than required will be selected. However, a borescope having an insertion tube that is longer than necessary for the inspection presents unnecessary handling and packaging difficulties and is more costly than a similar borescope having a shorter insertion tube. The diameter of the insertion tube selected for use presents perhaps an even greater concern than the length of the insertion tube. Many inspection activities require the insertion tube to navigate a tortuous path from an access port to the test area. A relatively larger diameter insertion tube generally will exhibit reduced flexibility when compared to a relatively smaller diameter insertion tube, thus making it more difficult to manipulate the larger diameter tube. Accordingly, there is a tendency for the user to select a borescope having an insertion tube diameter smaller than necessary to ensure that all test areas can be accessed, even in the event of encountering an unexpected obstruction during the inspection. However, the present inventors have noted that insertion tube field failure rates are closely and dramatically associated with the tube diameter. For example, in the range of 5-8 mm diameter insertion tubes, it is not unknown to experience a doubling of the failure rate for each 1 mm reduction in tube diameter.

Figure 1:
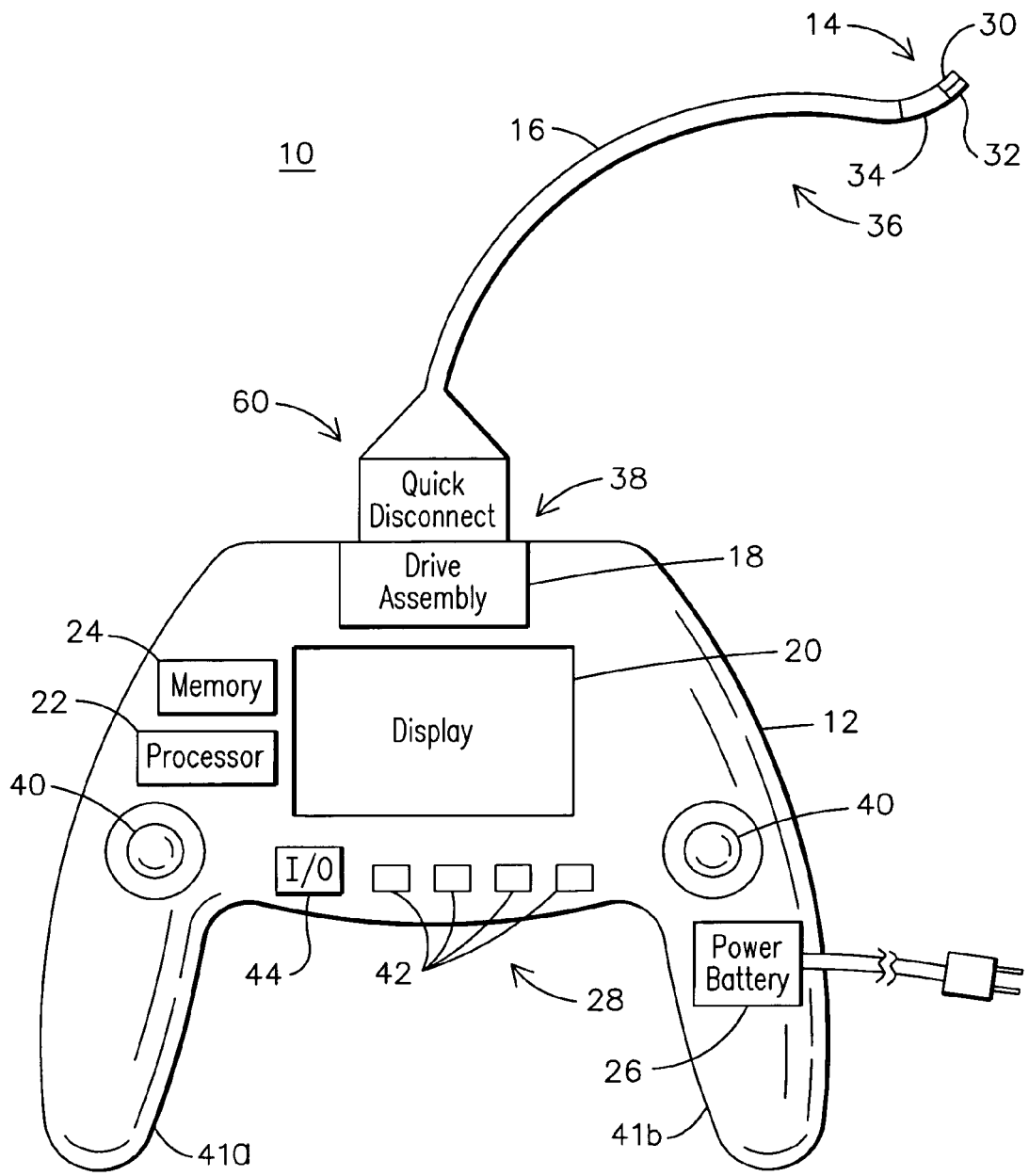
FIG. 1 is a schematic illustration of a remote viewing apparatus in accordance with the present invention.

The present inventors have developed a remote vision apparatus that innovatively addresses many of the problems experienced with prior art devices. FIG. 1 is a schematic illustration of one embodiment of an improved remote viewing apparatus 10. Advantageously, the remote viewing apparatus 10 incorporates quick-disconnect interconnectivity of its constituent parts to provide flexibility during the configuration of the apparatus and to facilitate field reparability in the event of a component failure.

The remote viewing apparatus 10 includes a control unit 12, an inspection head 14, and an insertion tube 16 connected therebetween. The control unit 12 is preferably sized and shaped to allow it to be hand held and manually manipulated. Associated with the control unit 12 are a drive assembly 18, a display 20, a processor 22 and associated memory 24, a power supply 26 and various input/output devices 28. The inspection head 14 is configured for imaging objects, such as a generally inaccessible interior area of a turbine engine. The inspection head 14 includes a camera 30 and a light source such as light emitting diodes (LEDs) 32 which may be removably attached to an articulated tip 34 at a distal end 36 of the insertion tube 16. As will be described more fully below, remote viewing apparatus 10 is modularized to facilitate the configuration of the unit for various inspection activities and to facilitate the repair of the unit in a field inspection environment.

The insertion tube 16 is removably connected to the control unit 12 via a connector assembly 38 that conveniently may be engaged and disengaged in a field-testing environment. The connector assembly 38 includes mating first and second connector halves 38a, 38b (FIG. 2) that function, when connected, to convey mechanical power from the drive assembly 18 to the articulated tip 34, and to convey electrical power from the control unit 12 to energize the light source 32 and the camera 30, and to convey video signals from the camera 30 to the display device 20. The connector assembly 38 allows the apparatus 10 to be configured with any number of different insertion tubes 16 having differing lengths and/or cross-sectional dimensions, i.e., diameters, to optimize the performance of the unit for a particular inspection activity. The insertion tube 16 initially used at a job site may be selected to have as large a diameter as practical in order to maximize the durability of the remote viewing apparatus. If the larger-sized insertion tube cannot be successfully used, an insertion tube 16 having a smaller diameter may be field-installed for completing the inspection. Similarly, should the insertion tube 16 fail for any reason, a replacement insertion tube 16 may be installed by simply disconnecting the second connector half 38b of the failed tube from the first connector half 38a at the control unit 12 and reconnecting the replacement tube which is fabricated with a compatibly configured mating second connector half 38b.

Other component parts of the remote viewing apparatus 10 may be conveniently replaced in the event of component failures. For example, camera 30 and light source 32 may be connected to the articulated tip 34 via plug-in connectors. The camera 30 in one embodiment may be a 4.3 mm SUPER HAD CCD brand color camera sold by Sony Corporation. The light source 32 in one embodiment may be light emitting diodes with a total output of about 2,600 lumens. Alternatively, the light source 32 may be a fiber light guide for transmitting light energy through the insertion tube 16 to the inspection head 14, for example, for transmitting light from a light source at the control unit 12 to the inspection head 14.

Software for imaging processing and other desired functions of the remote viewing apparatus 10 may reside in an easily-replaceable memory device 24, for example, a known type of memory card such as a flash card or memory stick, for execution by processor 22. The software may include an operating system, image acquisition and control, file management, digital zoom, text annotation, graphic annotation, articulation control, light source control, electronic distance measurement, and/or auto-detect/recognition functions as may be desired for a particular application.

The control unit 12 may be ergonomically designed for comfortable hand-held operation. Its size and shape may be similar to current video game controllers and may, for example, include left and right handle portions 41a and 41b (FIG. 1) for support by the left and right hands of an operator. The monitor 20 may be a high-resolution liquid crystal display (LCD). One or more joystick controls 40 may be provided for user input for control of the movement of the articulated tip 34. One or more button switches 42 may be provided for further user input to processor 22 and/or for manipulation of the inspection head 14. Accordingly, the control unit 12 is hand-holdable for an operator to comfortably hold the control unit 12 between the operator's hands while also manipulating the joystick controls 40 and switches 42. A remote input/output (I/O) function 44, such as a USB port or RF connection, may be used for communication between the control unit 12 and remote locations such as a remote viewing station. Batteries and/or A/C power may be used to energize a power supply 46.

Figure 2:
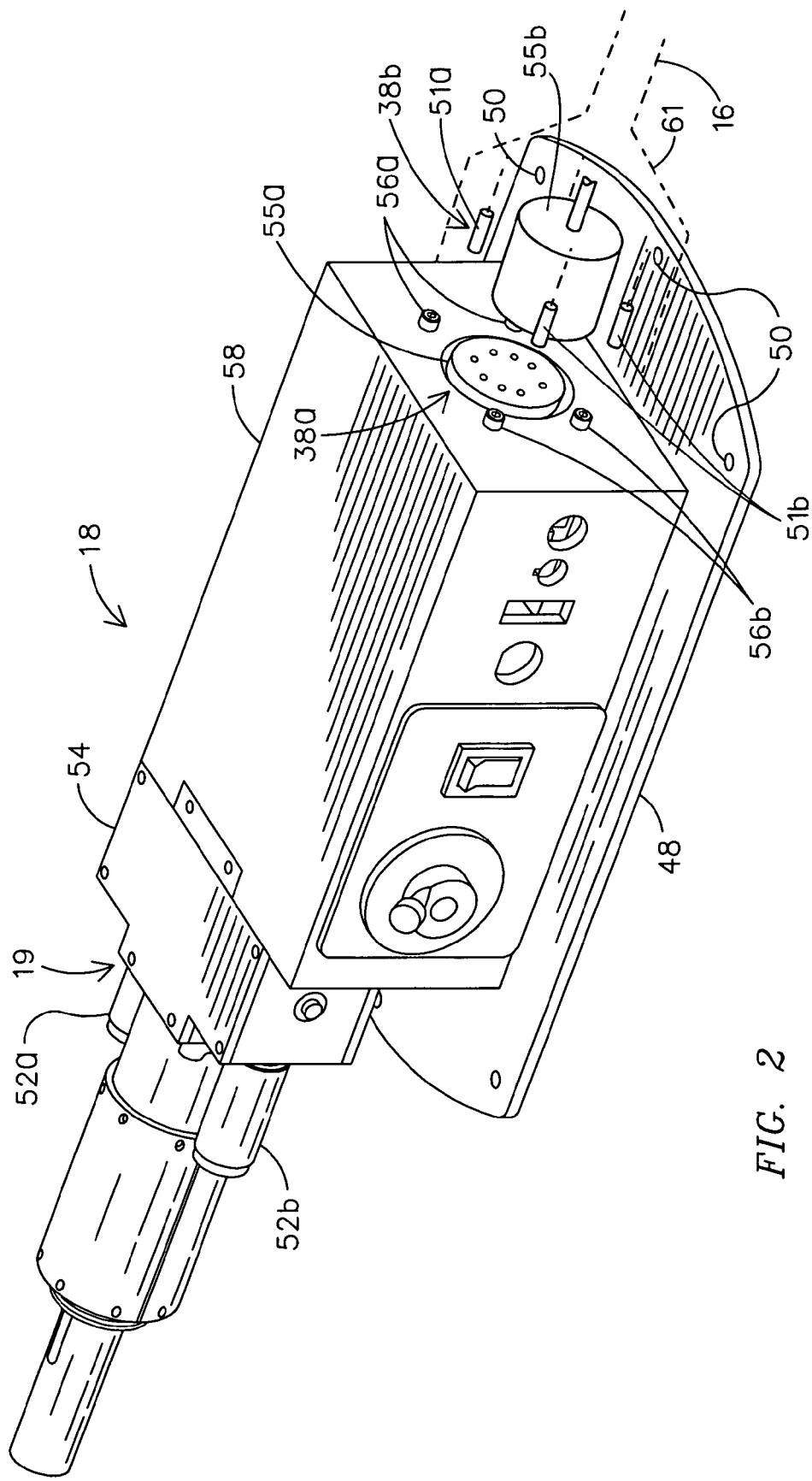
FIG. 2 is a perspective view of an articulated tip drive assembly for the remote viewing apparatus of FIG. 1.

FIG. 2 is a perspective view of one embodiment of a drive assembly 18 for moving the articulated tip 34. The drive assembly 18 may be removably attached to the control unit 12 via a mounting plate 48 and fasteners (not shown) passing through mounting holes 50. The drive assembly 18 of this embodiment includes two servomotors 52a, 52b connected via respective gear trains housed in a gear box 54 to respective pairs of cable pull racks 56a, 56b. The gear trains are arranged so that rotational movement of one of the motors 52a or 52b results in respective coordinated pull/push linear movement of the associated pair of cable pull racks 56a or 56b.

Figure 3:
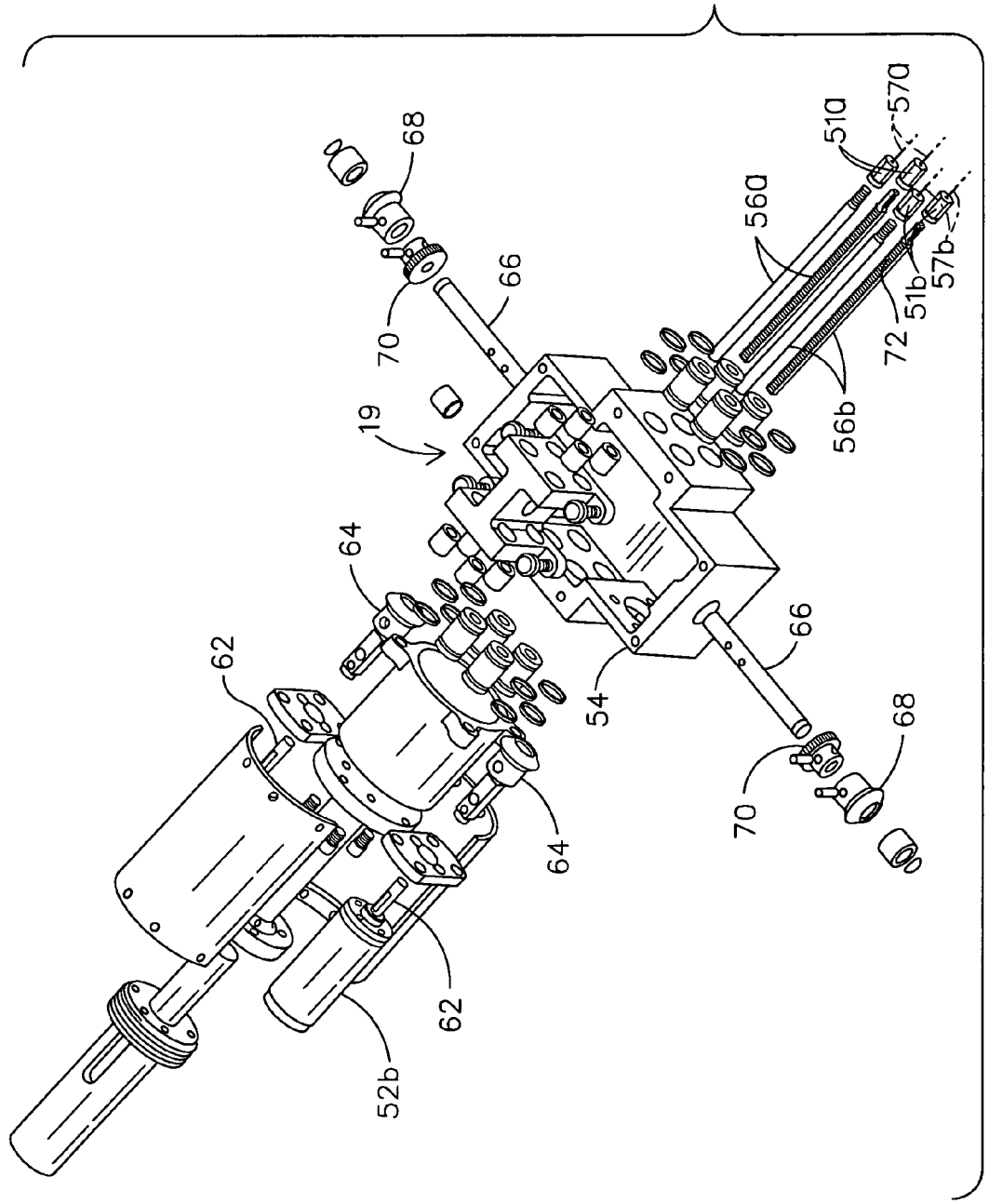
FIG. 3 is an exploded view of a drive portion of the drive assembly of FIG. 2.

FIG. 3 is an exploded view of a drive portion 19 of the drive assembly 18 of FIG. 2 illustrating component part details. Drive motors 52a, 52b each provide rotary motion via respective output shafts 62 to a respective motor side miter gear 64. Rotary power is transferred form the motor side miter gears 64 to respective drive shafts 66 via respective shaft side miter gears 68 engaged with the motor side miter gears 64. A spur gear 70 attached to each respective drive shaft 66 imparts linear motion in opposing directions to the respective pair of cable pull racks 56a and 56b. The cable pull racks 56a, 56b are formed to include teeth 72 that interface with respective top and bottom sides of the spur gears 70 to provide the coordinated opposing motion.

Referring to FIGS. 2 and 3, the pairs of pull racks 56a, 56b are detachably attached to respective ends of cable pairs 57a, 57b passing through the insertion tube 16 via the connector assembly 38 to provide articulation in both the x-axis (e.g. cable pair 57a) and y-axis (e.g. cable pair 57b) to the distal end of the articulated tip 34. The first connector half 38a is disposed at a distal end of a drive assembly housing 58 supported on the mounting plate 48, and includes ends of the pairs of pull racks 56a, 56b and an electrical connector element 55a.

The second connector half 38b is preferably disposed within a connector housing 61 located at the proximal end 60 of the insertion tube 16 and comprises pairs of cable end couplings 51a, 51b for coupling to the ends of the pairs of pull racks 56a, 56b and an electrical connector element 55b for coupling with the electrical connector element 55a. The pairs of cable end couplings 51a, 51b are attached to the ends of respective cable pairs 57a, 57b. Distal ends of the pairs of pull racks 56a, 56b are each threaded, and the pairs of the cable end couplings 51a, 51b each include threaded end portions, such as threaded apertures opposite from respective cables of the cable pairs 57a, 57b, for rotatable threaded engagement with the pairs of pull racks 56a, 56b, whereby the cable pairs 57a, 57b are actuated in longitudinal movement with longitudinal movement of the respective pairs of pull racks 56a, 56b.

It may be seen that the drive assembly 18 is supported on the control unit 12 as a replaceable component, permitting ready replacement in the event of a failed drive assembly element, such as, for example, a failure of a servomotor. In particular, the connection of the drive assembly 18 to the insertion tube 16 may be readily detached or reattached at the connector assembly 38 for efficient replacement of the drive assembly 18 as separable component from both the control unit 12 and the insertion tube 16.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A remote viewing device comprising:
    a control unit sized and shaped to be hand held, said control unit comprising:
        left and right handle portions for support by left and right hands of an operator;
        a display device; and
        a drive assembly removably mounted to and supported on a remaining portion of said control unit, said drive assembly for providing mechanical power;
    an insertion tube comprising a proximal end and an articulated tip at a distal end;
    an inspection head associated with said articulated tip, said inspection head configured for imaging the interior of an object; and
    a connector assembly removably engaged with said control unit and removably interconnecting said control unit and said proximal end of said insertion tube, said connector assembly operable, when connected, to convey the mechanical power from said drive assembly for moving said articulated tip in response to a user input at said control unit, and to convey images from said inspection head to said display device, wherein said user input is performed by the operator while grasping said control unit.

2. The remote viewing device of claim 1, wherein said connector assembly comprises a first connector half supported on said drive assembly and a second connector half supported on said insertion tube for detachable connection to said first connector half.

3. The remote viewing device of claim 1, wherein said insertion tube comprises a plurality of cables for conveying the mechanical power from the proximal end to the articulated tip, and said drive assembly includes cable pull racks for actuating said cables.

4. The remote viewing device of claim 3, including a coupling on the end of each said cable, and each said coupling being detachably engaged on the end of a respective cable pull rack to define detachable connections between said cables and said cable pull racks.

5. The remote viewing device of claim 3, wherein said drive assembly comprises a pair of motors, each said motor actuating a respective pair of said cable pull racks in longitudinal movement within said drive assembly.

6. The remote viewing device of claim 5, wherein said drive assembly includes a mount element for removable attachment to a side of said remaining portion of said control unit.

7. The remote viewing device of claim 6, wherein said drive assembly comprises a housing enclosing said cable pull racks and said housing is supported on said mount element for said removable attachment to said remaining portion of said control unit.

8. The remote viewing device of claim 1, wherein said inspection head comprises a camera and a light source.

9. The remote viewing device of claim 8, wherein said camera and said light source are removably attached to said inspection head.

10. The remote viewing device of claim 8, wherein said connector assembly is further operable, when connected, to convey electrical power to said camera and said light source.

11. The remote viewing device of claim 1, including a memory device removably attached to said control unit, said memory device including operating system software for use by a processor in said control unit to control an image processing operation.

12. The remote viewing device of claim 11, wherein said memory device comprises a memory card.

\* \* \* \* \*